US006347548B1

(12) United States Patent
Powrie

(10) Patent No.: US 6,347,548 B1
(45) Date of Patent: Feb. 19, 2002

(54) APPARATUS FOR AND METHOD OF MONITORING A ROTATING MACHINE

(75) Inventor: Honor Powrie, Southampton (GB)

(73) Assignee: Stewart Hughes Limited, East Leigh (GB)

(*) Notice: Subject to any disclaimer, the term of this patent is extended or adjusted under 35 U.S.C. 154(b) by 0 days.

(21) Appl. No.: 09/291,509

(22) Filed: Apr. 14, 1999

(30) Foreign Application Priority Data

Apr. 17, 1998 (GB) .............................................. 9808220

(51) Int. Cl.⁷ .............................................. G01M 15/00
(52) U.S. Cl. ...................................................... 73/162
(58) Field of Search .............................. 73/162, 118.1, 73/86, 53.05, 53.07, 61.42; 324/457, 513, 71.2

(56) References Cited

U.S. PATENT DOCUMENTS 4,625,280 A * 11/1986 Couch 5,182,596 A * 1/1993 Nakazawa et al. .......... 324/457

OTHER PUBLICATIONS

International Patent Application No. PCT/GB 91, 02112, published as WO 92/09886 on Jun. 11, 1992.
International Paent Application No. PCT/GB 96/01407, published WO 97/ 01093 on Jan. 9, 1997.

* cited by examiner

Primary Examiner—Robert Raevis
(74) Attorney, Agent, or Firm—Irwin Ostroff

(57) ABSTRACT

One or more electrostatic sensors 3 and a tacho generator 2 are provided in a machine 1 such as a gearbox. Signals from the sensors 3 and the tacho generator 2 are processed by a signal processing circuit 6 to monitor for abnormal interaction between plural interacting components of the machine 1. The signal from the tacho generator 2 may be used by the signal processing circuit 6 to produce a signal which is an average of the electrostatic activity at the interacting components over a cycle of the machine. Such an averaged signal will contain enhanced components relating to electrostatic activity relating to the cycle of the machine.

19 Claims, 3 Drawing Sheets

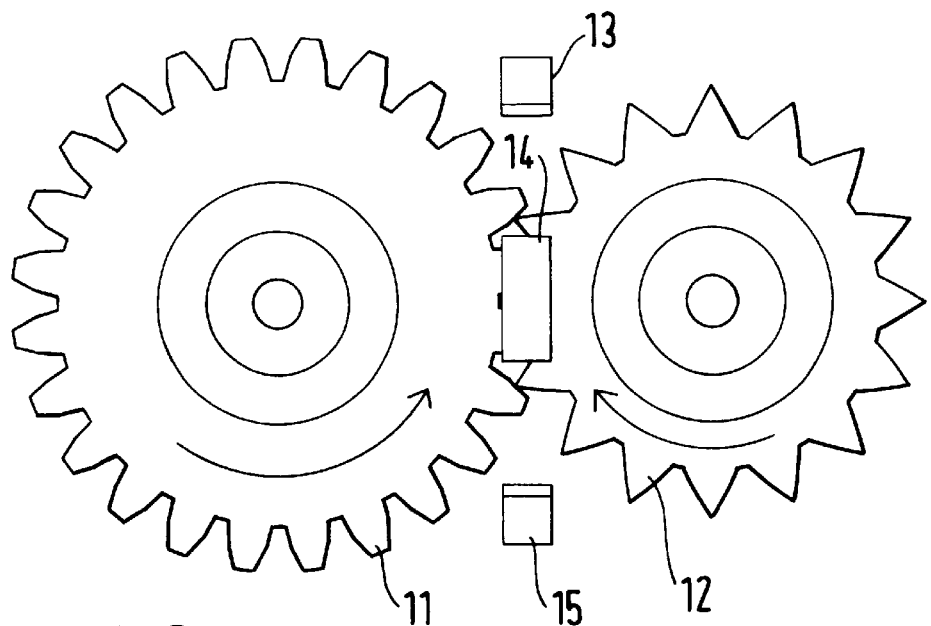
FIG.2
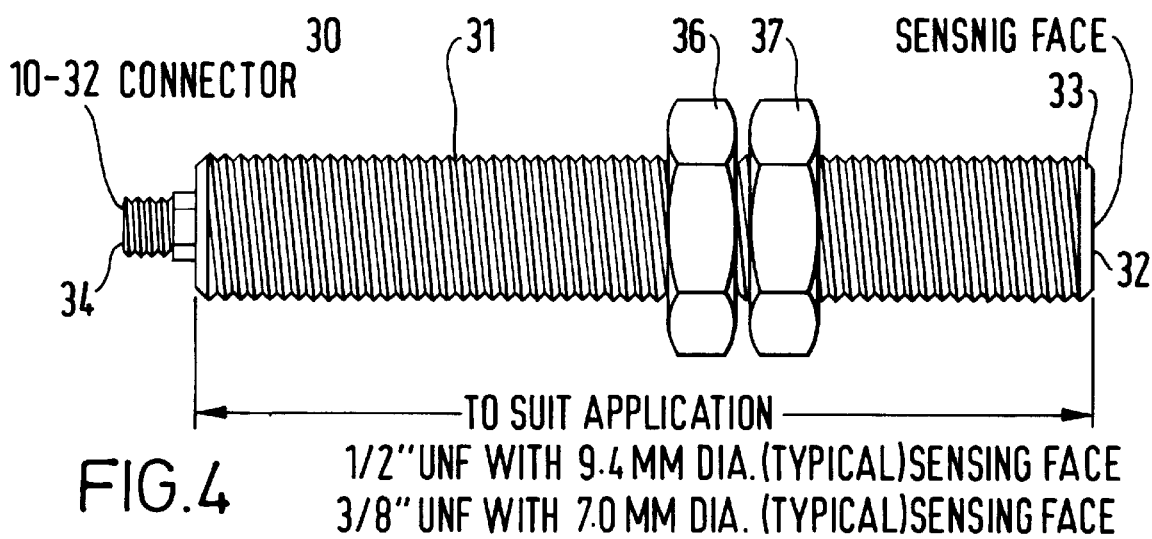
FIG.4   TO SUIT APPLICATION
1/2"UNF WITH 9.4 MM DIA.(TYPICAL)SENSING FACE
3/8"UNF WITH 7.0 MM DIA. (TYPICAL)SENSING FACE

APPARATUS FOR AND METHOD OF MONITORING A ROTATING MACHINE

FIELD OF THE INVENTION

The invention relates to an apparatus for and method of monitoring a machine. The invention is well suited to the monitoring of wear in such machines as gearboxes but can also be applied to other mechanical systems in which rotating parts are present. As used herein the term "rotating" is intended to encompass any machine whose operation is cyclic in nature and thus includes among other things reciprocating machines.

BACKGROUND OF THE INVENTION

In International Patent Application No. PCT/GB 91/02112 published as WO 92/09886, the teachings of which are incorporated herein by reference, there is described a system for monitoring debris in a fluid. The system comprises at least one electrostatic sensor for producing a signal representing electrostatic charge associated with the fluid moving past the sensor and with debris and/or impurities carried by the fluid. The signal from the sensor is conditioned by a signal conditioner and the conditioned signal is processed by a signal processor together with another signal representing at least the charge associated with the moving fluid in order to produce a signal representing the electrostatic charge associated with the debris and/or impurities. In practice two electrostatic sensors are used at spaced apart locations and the signals therefrom are processed, i.e. correlated, in order to identify the existence of debris in the moving fluid. The system is extremely useful for detecting wear in machines because machine wear causes charge carrying particles to be generated which can be detected by the system.

In International Patent Application No. PCT/GB 96/01407 published as WO 97/01093, the teachings of which are incorporated herein by reference, there is described an apparatus for monitoring a lubricant in a machine. The apparatus comprises electrostatic sensors for producing signals representing electrostatic activity in a machine lubricant and a temperature sensor for producing a signal representative of the temperature of the lubricant. A signal processor is arranged to compensate for temperature related changes to the signals from the electrostatic sensors in response to the signal from the temperature sensor, and to process the signals from the electrostatic sensors to detect an electrostatic activity precursor that is indicative of an impending wear event in the machine.

SUMMARY OF THE INVENTION

The present invention resides in the discovery that there is a change in electrostatic activity in a machine at the location of a part whose operation is cyclic, for example a rotating or reciprocating part, when that part is experiencing an abnormal loading.

In one aspect the invention provides an apparatus for monitoring a machine, the apparatus comprising a sensor for producing a signal representing electrostatic activity in the vicinity of plural interacting components of the machine, a tacho generator for generating a tacho signal representing a cycle of the machine, and a signal processor for processing the signal from the sensor together with the tacho signal to monitor for abnormal conditions in the interaction between the plural components.

In another aspect the invention provides a method of monitoring a machine, the method comprising producing a signal representing electrostatic activity in the vicinity of plural interacting components of the machine, generating a tacho signal representing a cycle of the machine, and processing the signal together with the tacho signal to monitor for abnormal conditions in the interaction between the plural components.

In another aspect the invention provides a method of and system for monitoring operation of a machine by detecting cyclic electrostatic activity at interacting components of the machine indicative of an abnormal loading or wear thereat.

In another aspect the invention provides a method of and system for monitoring a machine lubricating fluid, in which method and an electrostatic signal is processed depending on a cycle of the machine to identify machine cycle dependent electrostatic activity at a selected location within the machine.

An ability to detect such a change in electrostatic activity enables potential problems with the running of a machine to be identified before a failure occurs in the machine. Thus, wear or even catastrophic failure in a machine may be avoided as a result of the advance warning enabled by the invention.

The above and further features of the invention are set forth with particularity in the appended claims and together with advantages thereof will become clearer from consideration of an exemplary embodiment of the invention given with reference to the accompanying drawings in which:

BRIEF DESCRIPTION OF THE DRAWINGS

FIG. 2 is a schematic diagram showing gears and sensors within a rotating machine;

FIG. 4 shows an example of an electrostatic sensor.

DETAILED DESCRIPTION OF THE DRAWINGS

Figure 1:
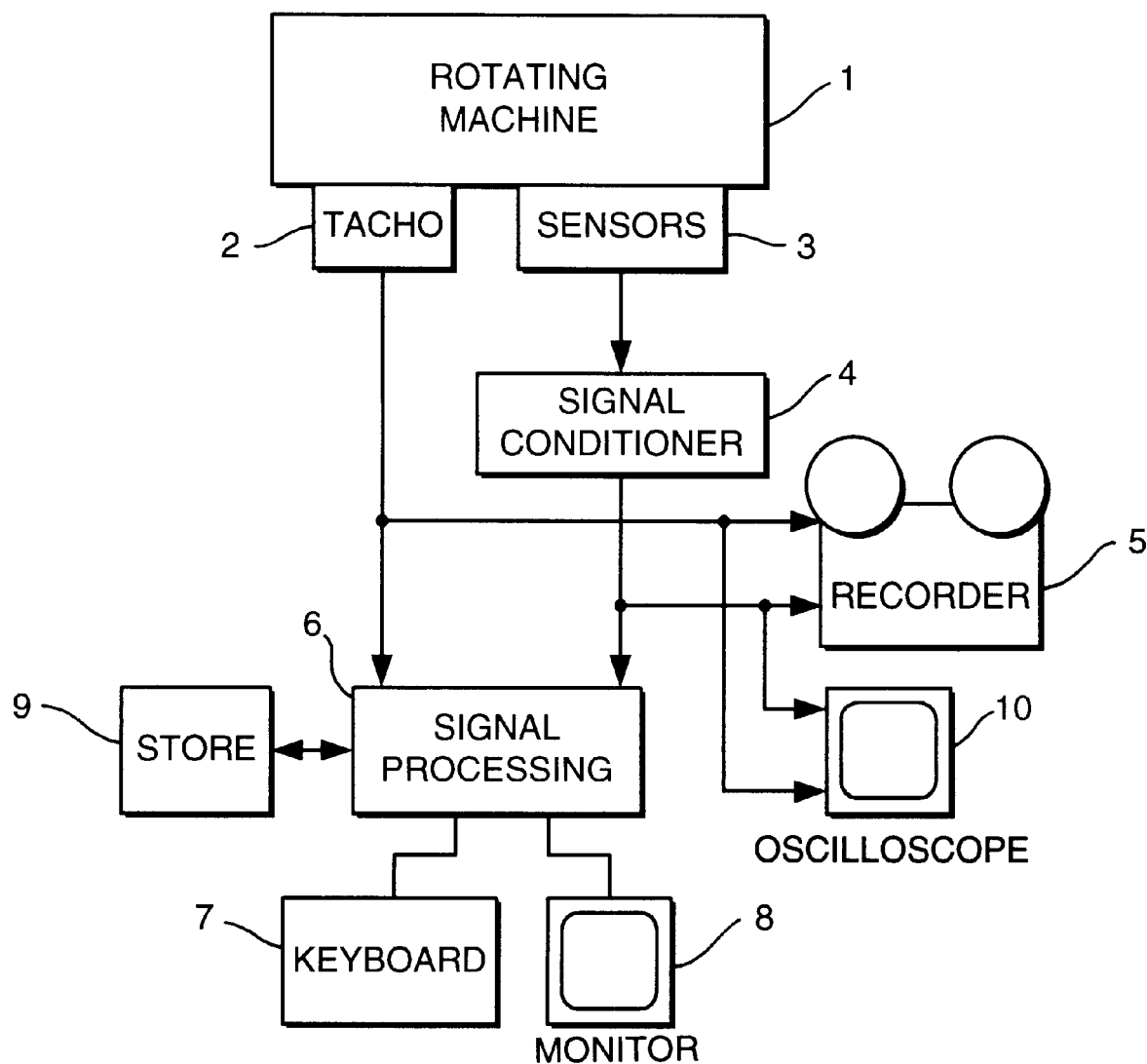
FIG. 1 is a schematic diagram of a system for monitoring operation of a rotating machine.

Turning now to FIG. 1 of the accompanying drawings there is shown a rotating machine 1 such as a gearbox having a tacho generator 2 and other sensors 3 mounted thereto. The tacho generator 2 generates a once per revolution signal as the rotating machine rotates. The sensors 3 are provided for sensing electrostatic charge and any suitable form of sensor may be used. The sensors 3 are connected to a signal conditioner 4 which is provided to perform a preliminary conditioning of the signals from the sensors 3. The signals from the sensors 3 are induced by electrostatic charge passing the sensors. As such the signals tend to be weak and one purpose of the signal conditioner 4 is to give robustness to the signals. The signal conditioner 4 may also act as a coarse filter to remove noise from the signals and may even include integrating and differentiating circuits if so required. Signal conditioning and signal conditioning circuits are per se well known and will not be described in any greater detail herein.

Conditioned signals from the signal conditioner 4 are recorded by a tape recorder 5 or other bulk signal-storage medium for subsequent analysis by a signal processing circuit 6. The signal processing circuit 6 may be a dedicated circuit or it may be a general purpose computer, suitably programmed.

FIG. 1 shows a keyboard 7 and monitor 8 connected to the signal processing circuit 6 to enable user interaction there-with. A store 9 is also provided for use by the signal processing circuit 6. The signal processing may be performed by the signal processing circuit 6 on-line and in real time. Results of the signal processing can be displayed on the monitor 8 in any suitable form for inspection by a user. An oscilloscope 10 may also be connected to the tape recorder to allow a user to inspect the conditioned signals from the signal conditioner 4 prior to processing by the signal processing circuit 6.

Among other things the signal processing circuit 6 processes the signals to determine the electrostatic activity level represented by the conditioned signals from the sensors 3. The activity level is determined by calculating a rolling RMS value from the conditioned signals. Alternatively or additionally such methods as high and/or low pass filtering and/or Fast Fourier Transforms (FFTs) may be used by the signal processing circuit or computer to determine the electrostatic activity level represented by the conditioned signals.

FIG. 2 shows a detail of two gears 11, 12 within a gearbox, i.e., the rotating machine 1. Three sensors 13, 14, 15 are located around the position at which the two gears 11, 12 intermesh with each other. The three sensors 13, 14, 15 correspond to the sensors 3 represented in FIG. 1. Although three sensors are shown in FIG. 2, a single sensor is sufficient, as should become clear from the description that follows.

The sensors 13, 14, and 15 are electrostatic sensors. During running of the gearbox, or indeed any rotating machine a background electrostatic charge will be present. The background charge is generated from several sources including the meshing together of gears, the rotation of shafts on bearings and the aeration of lubricant within the machine. When the machine is running normally the background charge will be detected as a noise signal by the sensors 13, 14, and 15. Such a noise signal contains no useful information and therefore is removed by the signal conditioner 4 and the signal processing circuit 6. Only frequencies associated with the rotation of the machine are of interest and therefore the signal conditioner 4 may include filters for filtering out noise outside the frequency range of interest. Noise reduction techniques such as described in the aforementioned WO 92/09886 may also be used to increase the signal to noise ratio of the signals. If necessary, any temperature related sensitivity in the sensors 13, 14, and 15 may be compensated for by providing a thermocouple (not shown) at a suitable position within the rotating machine.

It has been found that there is a change in electrostatic activity in a machine at a rotating part when that part is experiencing an abnormal loading. In the case of a gearbox the abnormal loading may for example be a high level of wear on a particular tooth on a given gear, caused for example by damage by a foreign object, imperfections in the material of the gear or misalignment of the gear. However the abnormal loading is caused, its effect will be to change (normally by increasing) the electrostatic activity where the abnormal loading occurs. In the case of a gearbox this will typically be where gears mesh with each other.

Although a single sensor may be employed to sense electrostatic activity, the use of two or more spaced apart sensors is advantageous. Two or more sensors enable more specific positioning of the fault or abnormal loading that is the cause of the increase in electrostatic activity. When signals from the sensors 13, 14, and 15 are processed in conjunction with the tacho signal from the tacho generator 2, the cyclic nature of the gearbox enables the position of the fault to be determined to an accuracy of one side of a tooth on a given gear.

Typical of rotating machines, a gearbox is a noisy environment. Even when a gearbox is running normally there will be a relatively high level of electrostatic noise which will be sensed by the sensors 13, 14, and 15. When a fault occurs the resulting increase in electrostatic activity may be relatively low. It would not be unusual for the fault-related electrostatic signal (the signal of interest) to have a level similar to that of the background noise. However, the cyclic nature of the fault means that the signal of interest will also be cyclic in nature. This fact can be used by the signal processing circuit 6 to enable the signal of interest to be extracted from the background noise.

Figure 3:
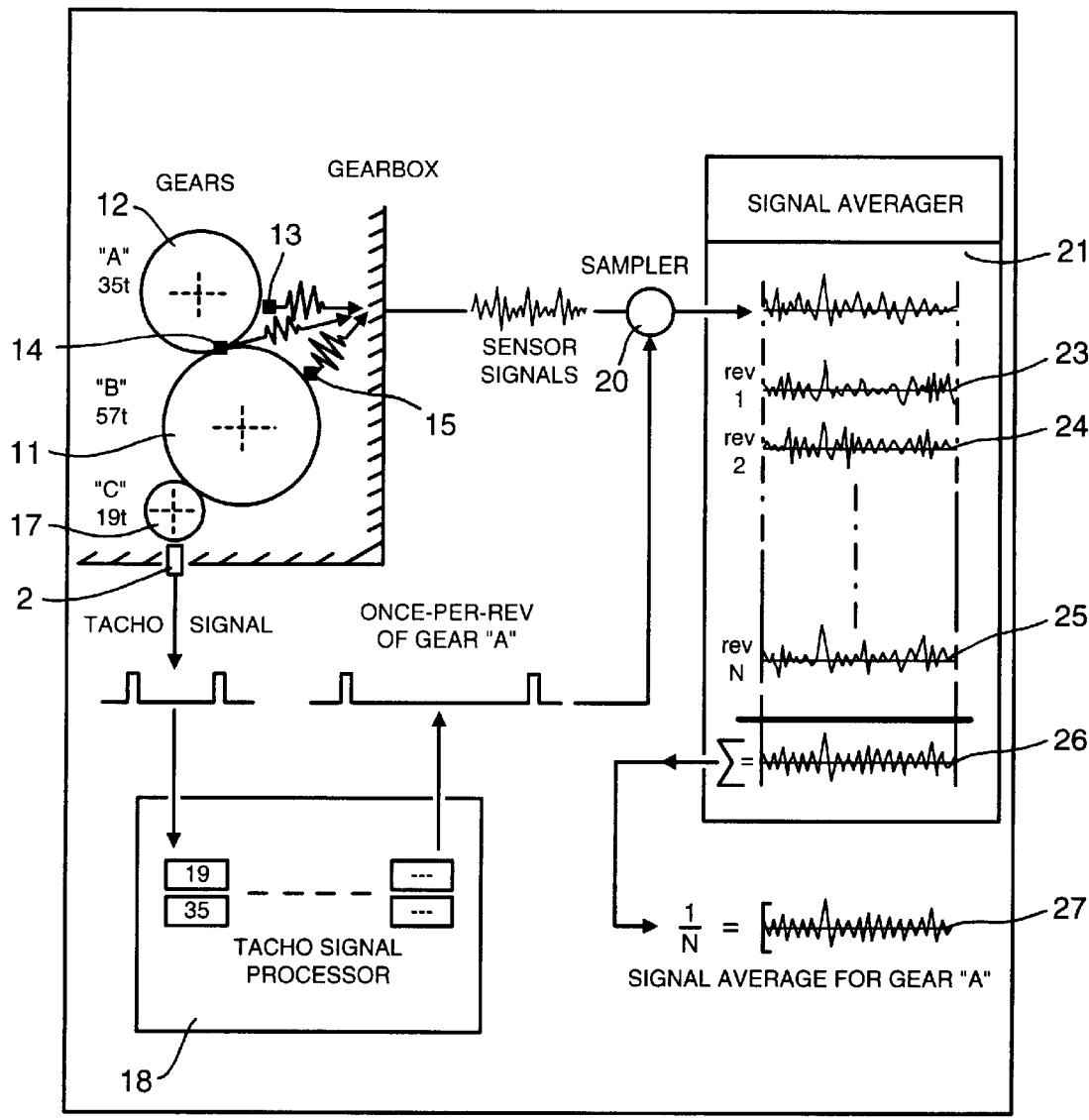
FIG. 3 is a schematic diagram representing signal processing used to extract signals of interest from sensed signals.

FIG. 3 represents the signal processing used to extract the signal of interest from the signals received from the sensors 13, 14, and 15. As shown in FIG. 3 the tacho generator 2 is arranged to generate a once-per-revolution signal as a shaft or gear 17 (referred to herein as a "reference gear") within the gearbox rotates. The tacho signal is input to a tacho signal processor 18 which may be provided as a subcomponent of the signal processing circuit 6 shown in FIG. 1. The tacho signal processor 18 is arranged to convert the signal generated by the tacho generator 2 from a once-per-revolution signal associated with the reference gear 17 to a once-per-revolution signal associated with the gear of interest, namely gear 11 or 12 in the example shown in FIG. 3. The ratio of the gears is known and it is therefore a simple matter to convert the tacho signal from the tacho generator 2 into a tacho signal for the gear of interest. For example, if the reference gear 17 has 19 teeth and the gear 11 has 57 teeth, then the tacho signal processor 18 will adjust the tacho signal from the tacho generator 2 by the ratio 19:57 in order to arrive at a once per revolution signal for the gear 11. The tacho signal processor 18 can be set to generate a once-per-revolution signal for any gear within the gear box simply by adjusting the ratio to correspond to that between the reference gear 17 and the gear of interest.

The once-per-revolution signal from the tacho signal processor 18 is input to a sampler 20 which also receives the signals from the sensors 13, 14, and 15. The sampler 20 is arranged to "chop" the signals from the sensors into discrete signal sections corresponding to each single revolution of the gear of interest, e.g., gear 11. That is to say, each discrete signal section is of a duration corresponding to the period for the gear of interest to rotate through 360°. The chopped signal sections from the sampler 20 are input to a signal averager 21, which is arranged for each sensor 13, 14, 15 to sum together each signal section over a number N of revolutions of the gear 11 of interest. Graphical representations of N chopped signal sections 23, 24, 25 from one of the sensors 13, 14, and 15, and of the sum 26 of those signals are depicted in the box representing the signal averager 21 in FIG. 3 of the drawings. An averaged signal 27 is calculated by dividing the summed signal 26 by the number N of chopped signal sections corresponding to a number N of revolutions of the gear 11 of interest.

Any suitable technology may be used to implement the sampler 20 and the signal averager 21. For example, the sampler 20 may comprise an analogue to digital converter (ADC) with associated control circuitry responsive to the once-per-revolution signal, and the signal averager may comprise a random access memory (RAM) for storing digital data representing the N chopped signal sections 23, 24, and 25. The RAM need not be particularly large, relatively speaking, because in most cases chopped signal sections for only five to ten revolutions is sufficient to enable desired information to be obtained pertaining to the gear 11 of interest. The summing of the chopped signal sections 23, 24, 25 and the division by N of the sum may be performed by a suitably programmed processor or by a dedicated circuit. The design of such technology is well known to those skilled in the art and need not be described in any greater detail herein.

The result of summing N chopped signal portions and dividing the summed signal by N is to suppress random or non-synchronous information (noise) and to provide a discrete signal representing the electrostatic activity for a full revolution (360°) of the gear of interest. Noise is random in nature, and therefore in the summing of the chopped signal sections the noise in the N different chopped sections will tend to cancel out. Electrostatic activity associated with the rotation of the gear 11 of interest, however, is cyclic, and therefore in the summing of the chopped signal sections the signal components associated with electrostatic activity will add together in a constructive way to increase the magnitude of the electrostatic signal components in the summed signal.

Thus the signal averager 21 serves to produce a summed signal which may be regarded as a signature of the electrostatic activity associated with the gear of interest. The signature signal is obtained for the gear of interest (in fact signature signals are obtained for each gear of interest) when the gear is known to be operating properly. The signature signal thus serves as a reference against which abnormalities may be detected. Once the signature signal has been obtained for the gear of interest, the signals from the sensors 13, 14, and 15 are monitored for changes from the norm as represented by the signature signal. Similar signature signals may of course be produced for other gears from other sensors (not shown) by making suitable changes to the tacho signal processor 18.

Several faults may cause a change in the electrostatic activity associated with a gear as compared with the signature signal of that gear. For example, if the electrostatic activity changes in only a small portion of a full revolution signal, this may indicate abnormal surface wear or damage to one tooth on the gear. A change in activity over a more significant portion of the full revolution signal may indicate damage to more than one tooth or may indicate that the gear is rotating off axis. In many cases such changes can be interpreted as a warning, thus enabling the gear to be inspected and adjusted or repaired before more expensive damage occurs to the gearbox. The signal processing circuit 6 may be arranged to generate a warning signal in the event of such a change. The warning signal may be linked to a suitable warning device on, say, a control panel associated with the running of the gearbox to alert a machine operator to the condition.

A single sensor located where two gears 11 and 12 mesh together, e.g., sensor 14 in FIGS. 2 and 3, enables changes in electrostatic activity at that location to be detected. Since the gears 11, 12 are of different sizes it is possible to determine where a fault lies by signal-averaging for the period of rotation of first one gear and then the other. The electrostatic activity signal component will rise out of the noise when the signal-averaging is performed at the period of rotation of the gear in which a fault lies.

Plural sensors facilitate the detection of a fault. Under some circumstances a gear tooth will wear on one side only. If two sensors 13, 15 are placed either side of where two gears 11, 12 mesh, the electrostatic activity associated with wear on one side will be detected as a stronger signal in one of the sensors as compared with the signal in the other of the sensors.

One or more sensor at each location where gears within the gearbox mesh provide signals from which components related to electrostatic activity may readily be extracted. Of course it is not always possible to fit so many sensors within a gearbox, especially if the gearbox has already been designed and installed, and the sensors are to be retrofitted. In some circumstances, depending on the harshness of the environment within the rotating machine and the desired level of accuracy at which faults are to be detected, it is possible to obtain useful signals from a few (one or more) sensors suitably located within the gearbox. The few sensors need not be located at or near the location where two gears mesh, but should be located where one or more meshes can be "seen" (i.e., the electrostatic activity thereat sensed).

FIG. 4 of the accompanying drawings shows an example of an electrostatic sensor 30 suitable for use in sensing electrostatic activity in a rotating machine. The sensor 30 comprises a threaded body 31 made from aluminium rod for example with a sensing face 32 at one end thereof electrically isolated from the body 31 by any suitable insulator 33. The sensing face 32 may be a copper film deposited on a glass reinforced plastic substrate which serves as the insulator 33. An electrical conductor (not shown) extends from the sensing face 32 through the body 31 to a connector 34 at the other end of the body. The connector 34 enables the sensor 30 to be connected to signal conditioning and/or processing circuitry such as that already described herein. A pair of nuts 36, 37 are provided on the threaded body 31 to enable the sensor 30 to be mounted at a convenient location on or within the rotating machine.

The sensor 30 is exemplary only. Electrostatic sensors are commonly available and any suitable known sensor may be used instead of or as well as the sensor 30.

Having thus described the present invention by reference to a preferred embodiment it is to be well understood that the embodiment in question is exemplary only and that modifications and variations such as will occur to those possessed of appropriate knowledge and skills may be made without departure from the spirit and scope of the invention and equivalents thereof.

What is claimed is:

1. Apparatus for monitoring a machine, the apparatus comprising:

a sensor for producing a signal representing electrostatic activity in the vicinity of plural interacting components of the machine;

a tacho generator for generating a tacho signal representing a cycle of the machine; and a signal processor for processing the signal from the sensor together with the tacho signal to monitor for abnormal conditions in the interaction between the plural components, the signal processor being arranged to process the signal from the sensor to detect a chance in the signal as representing abnormal conditions of one or more of the interacting components; and the signal processor being further arranged to process the signal from the sensor by dividing the signal into a number N of discrete signal sections corresponding to the cycle of the machine as determined by the tacho signal, then summing the discrete sections together to produce a summed signal, and dividing the summed signal by the number N to produce an averaged signal representing the electrostatic activity at the interacting components for the cycle of the machine, whereby noise signal components in the signal from the sensor are suppressed and signal components representing electrostatic activity relating to the cycle of the machine are enhanced.

2. The apparatus of claim 1 further comprising a signal conditioning circuit for improving the strength and signal to noise ratio of signals from the sensor, the signal conditioning circuit being connected to output conditioned signals to the signal processor.

3. The apparatus of claim 1, further comprising a recorder for recording signals from the sensor.

4. The apparatus of claim 1 further comprising an oscilloscope for displaying signals from the sensor.

5. The apparatus of claim 1 wherein the sensor comprises a first electrostatic sensor for sensing electrostatic activity at a first position in the machine and a second electrostatic sensor for sensing electrostatic activity at a second position in the machine.

6. The apparatus of claim 5 wherein the sensor further comprises a third electrostatic sensor at a third position in the machine.

7. The apparatus of claim 6 wherein the signal processor is operable to process the signals from each of the electrostatic sensors together with the tacho signal to identify abnormal wear at a specific position on one of the interacting components.

8. The apparatus of claim 5 wherein all of the electrostatic sensors are positioned in the same vicinity.

9. The apparatus of claim 1 wherein the machine is a gearbox and the interacting components are gears.

10. A method of monitoring a machine, the method comprising:

producing sensor signals representing electrostatic activity in the vicinity of plural interacting components of the machine;

generating a tacho signal representing a cycle of the machine; and processing the sensor signals together with the tacho signal to monitor for abnormal conditions in the interaction between the plural components, the sensor signals being processed by dividing the sensor signals into a number N of discrete signal sections corresponding to the cycle of the machine as determined by the tacho signal, then summing the discrete sections together to produce a summed signal, and dividing the summed signal by the number N to produce an averaged signal representing the electrostatic activity at the interacting components for the cycle of the machine, whereby noise signal components in the sensor signals are suppressed and signal components representing electrostatic activity relating to the cycle of the machine are enhanced.

11. The method of claim 10 further comprising conditioning the sensor signals.

12. The method of claim 10 further comprising recording the sensor signals.

13. The method of claim 10 further comprising displaying the sensor signals.

14. The method of claim 10 wherein the sensor signals comprise a first electrostatic signal representing electrostatic activity at a first position in the machine and a second electrostatic signal representing electrostatic activity at a second position in the machine.

15. The method of claim 14 wherein the sensor signals comprise a third electrostatic signal representing electrostatic activity at a third position in the machine.

16. The method of claim 14 wherein the electrostatic signals from each of the locations within the machine are processed together with the tacho signal to identify abnormal wear at a specific position on one of the interacting components.

17. Apparatus for monitoring a machine having cyclically operating components, the apparatus comprising;

a sensor for producing a sequence of signals representing electrostatic activity in the vicinity of operating components of the machine during respective cycles thereof;

means for generating cycle signals representing respective cycles of components of the machine; and a signal processor for processing the signals from the sensor together with the cycle signals to monitor for abnormal conditions in the operation of the components, the signal processor averaging the signals from the sensor over a number N of respective cycles of components of the machine to produce an averaged signal representing the electrostatic activity near the components for a cycle of the machine, whereby noise signal components in the signals from the sensor are suppressed and signal components representing electrostatic activity relating to a cycle of the machine are enhanced.

18. Apparatus for monitoring a machine, the apparatus comprising:

a sensor for producing a signal representing electrostatic activity in the vicinity of plural interacting components of the machine;

a tacho generator for generating a tacho signal representing a cycle of the machine; and a signal processor for processing the signal from the sensor together with the tacho signal to monitor for abnormal conditions in the interaction between the plural components; and the signal processor being further arranged to process the signal from the sensor by dividing the signal into a number N of discrete signal sections corresponding to the cycle of the machine as determined by the tacho signal, then summing the discrete sections together to produce a summed signal, and dividing the summed signal by the number N to produce an averaged signal representing the electrostatic activity at the interacting components for the cycle of the machine, whereby noise signal components in the signal from the sensor are suppressed and signal components representing electrostatic activity relating to the cycle of the machine are enhanced.

19. A method of monitoring a machine, the method comprising:

producing sensor signals representing electrostatic activity in the vicinity of plural interacting components of the machine;

generating a tacho signal representing a cycle of the machine;

processing the sensor signals together with the tacho signal to monitor for abnormal conditions in the interaction between plural components; and the sensor signals being processed by dividing the sensor signals into a number N of discrete signal sections corresponding to the cycle of the machine as determined by the tacho signal, then summing the discrete sections together to produce a summed signal, and dividing the summed signal by the number N to produce an averaged signal representing the electrostatic activity at the interacting components for the cycle of the machine, whereby noise signal components in the sensor signals are suppressed and signal components representing electrostatic activity relating to the cycle of the machine are enhanced.

* * * * *